United States Patent [19]

Braden et al.

[11] 4,131,802

[45] Dec. 26, 1978

[54] AUTOMATIC PATIENT TABLE HAVING MEANS FOR TRANSPORTING PATIENT ALONG A TABLE

[75] Inventors: Arthur B. Braden, Mentor; Thomas R. McBride, Chardon; Donald J. Styblo, Northfield Center; Samuel K. Taylor, Chardon; Joseph B. Richey, Shaker Heights, all of Ohio

[73] Assignee: Ohio-Nuclear, Inc., Solon, Ohio

[21] Appl. No.: 808,821

[22] Filed: Jun. 22, 1977

Related U.S. Application Data

[63] Continuation of Ser. No. 700,539, Jun. 28, 1976, abandoned.

[51] Int. Cl.² .................. A61B 6/02; G01N 23/08; G03B 41/16
[52] U.S. Cl. .................. 250/445 T; 250/363 S; 250/491; 269/322
[58] Field of Search .............. 250/453, 445 T, 445 R, 250/444, 439, 451, 449, 363 S; 144/288 R; 269/322

[56] References Cited

U.S. PATENT DOCUMENTS 3,974,388  8/1976  Distler et al. .................. 250/456

Primary Examiner—Alfred E. Smith
Assistant Examiner—T. N. Grigsby
Attorney, Agent, or Firm—Fay & Sharpe

[57] ABSTRACT

A versatile patient table system for transverse axial scanners employs front and rear tables with a spanning patient pallet for abdominal scans. A motorized conveyer belt on the front table increments the axial position of the patient. For brain scans the rear table and patient pallet are replaced by a head restraint assembly with a hinged headrest, check pad restraint members and a body pad which rests on the conveyer belt on the front table. In the automatic mode of operation, the belt moves either the body pad or the patient pallet out from the scanner in controlled increments triggered by the image processor. The hinged metal seam of the belt is used for indexing the extreme outward and inward positions.

18 Claims, 8 Drawing Figures

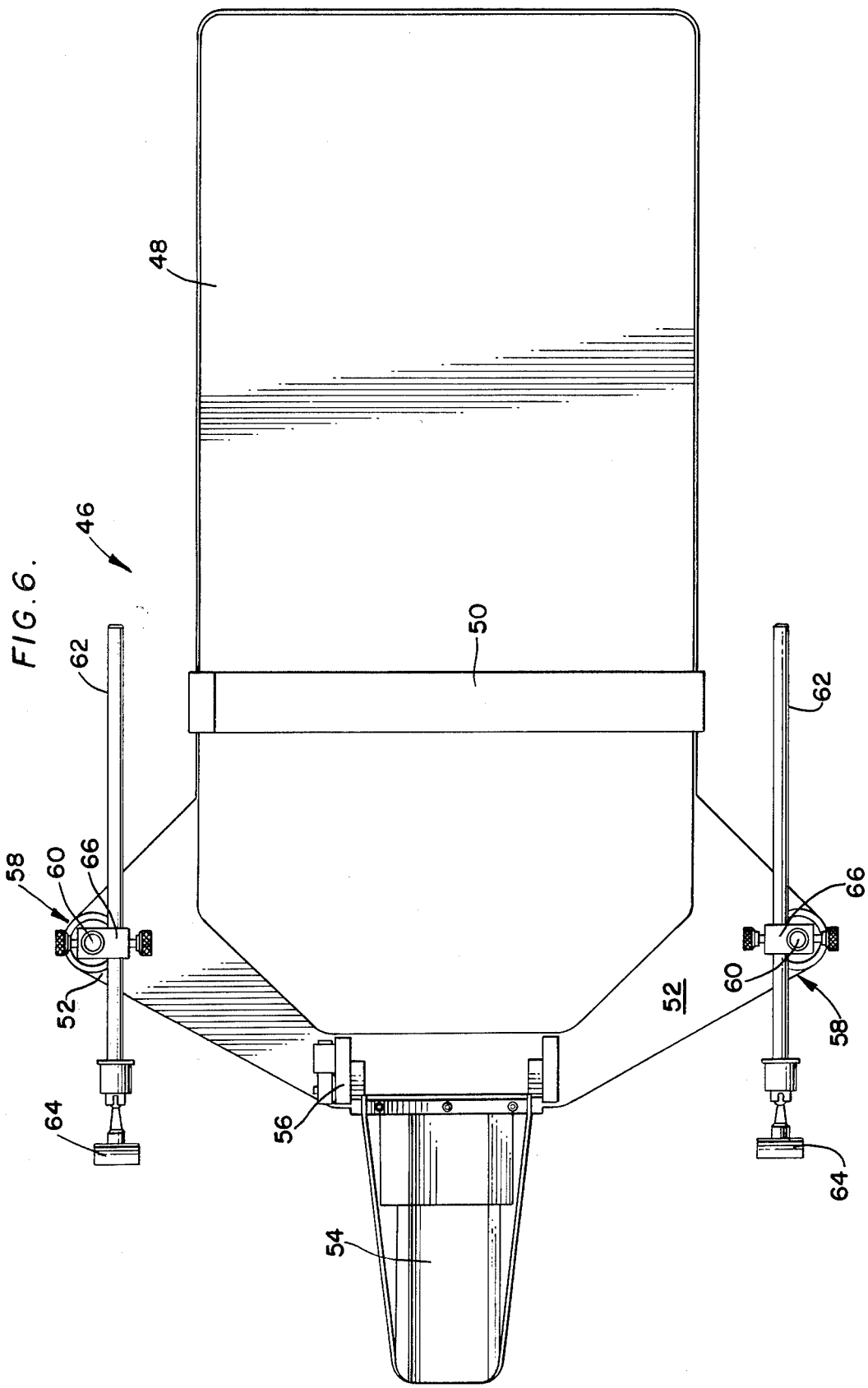

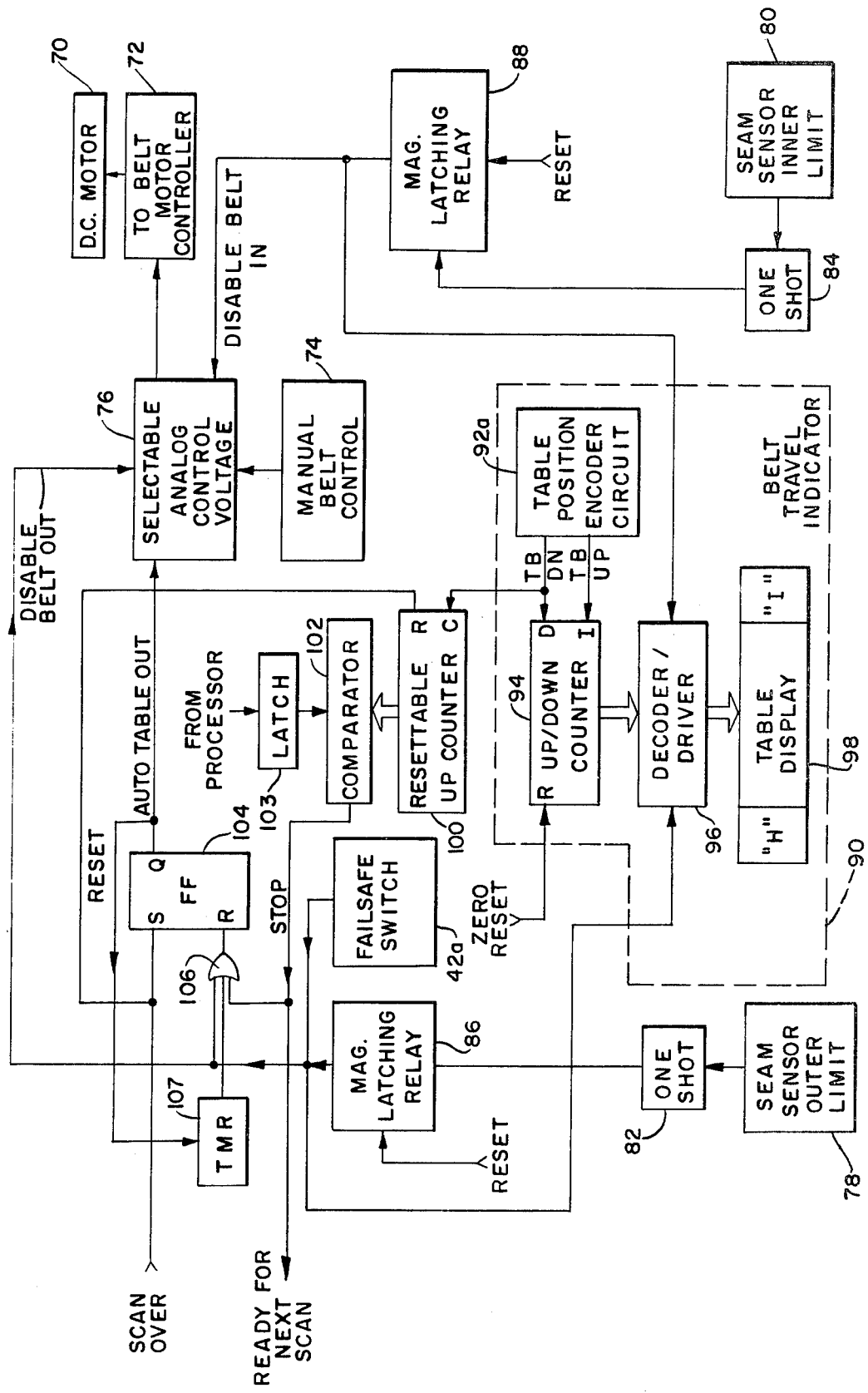

AUTOMATIC PATIENT TABLE HAVING MEANS FOR TRANSPORTING PATIENT ALONG A TABLE

This application is a continuation of Application Serial No. 700,539, filed June 28, 1976 and now abandoned.

BACKGROUND OF THE INVENTION

The invention relates to medical patient tables and more particularly to a patient support and positioning system used as part of an X-ray diagnostic medical instrumentation commonly known as a transverse, axial, computerized, tomographic X-ray scanner or "CT" scanner.

The CT scanner is becoming an increasingly popular tool for diagnosis of tumors and the like. Owing to good quality tomographic images with low dosage X-ray radiation without using angiogram techniques and other lengthy, uncomfortable procedures. the CT scanner has been swiftly accepted by the medical profession in brain and abdomical work. CT scanners have a circular opening of approximately 20 inches in which an X-ray beam and opposing scintillator-type detector are translated and rotated according to well-known procedures. An image processor such as the system used in CT scanners sold by Ohio-Nuclear, Inc., Model No. 50. It reconstructs a tomographic or cross-sectional image of the portion of the patient's body in the plane of the scan circle, using in part a construction algorithm.

From the standpoint of patient support, brain scans and abdominal scans are completely different. For the head scan, since only the head need be inserted into the scan circle, the remainder of the body may be supported from one side of the CT scanner apparatus. The abdominal scan presents a more difficult problem in that the patient must be inserted through the scan circle, thus requiring support structure of a different nature. Because of the low dosage radiation and the particular construction algorithms currently in use, non-air parts of the object being scanned should be entirely within the scan circle. Thin high density objects in the scan circle, particularly those with sharp edges, can produce streak artifacts in the image. Thus, it is important that the patient support in the scan circle be as narrow and lightweight as possible. If the table is to have automatic indexing means for taking scans at several axially displaced, adjacent locations, the problems of integrity of the indexing system become apparent: reliable accuracy and safety at a reasonable cost without operator interaction.

SUMMARY OF THE INVENTION

A versatile automatic patient support system for CT scanners includes movable front and rear tables, a removable patient pallet for abdominal scans and a removable head restraint assembly (replacing the patient pallet and rear table) for brain scans. For abdominal scans the front and rear tables are aligned on opposite sides of the apparatus defining the scan circle. A flexible thin plastic patient pallet spans the gap between the two tables with a narrow-waisted section of the pallet actually intersecting the scan circle. The front table has a motorized conveyor belt which drives the pallet in a manual or automatic-increment mode governed by the CT scanner's image processor. For brain scans, the rear table and patient pallet are replaced by a head restraint assembly which is placed on top of the front table, a thin plastic hinged headrest extends into the scan circle. The headrest and a pair of check pad restraint members are mounted to a restraint body pad which is mobilized by the front table conveyor belt. In the automatic mode of operation, either for brain scans or abdominal scans, automatic indexing results in precise incrementing of the patient pallet or head restraint assembly outward, i.e., away from the rear table. A hinged metal seam of the conveyor belt is used to index the extreme outward and inward positions. In addition, a failsafe bar switch prevents excursion of the patient beyond the end of the front table.

BRIEF DESCRIPTION OF THE DRAWINGS

FIG. 6 is a plan view of the detachable head restraint assembly of FIG. 4.

FIG. 7 is a functional block diagram representing a portion of the belt control system for the front table.

DESCRIPTION OF THE PREFERRED EMBODIMENT

Figure 1:
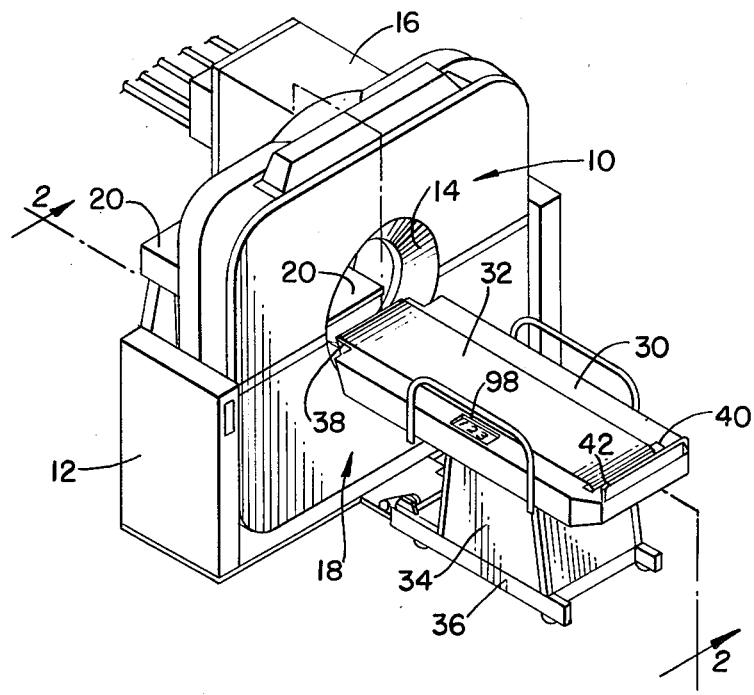
FIG. 1 is an oblique isometric view of a CT scanner with front and rear patient tables, according to the invention.

FIG. 1 shows a typical CT scanner having a gantry assembly 10 pivotally mounted on a U-shaped support structure 12 to allow tilting of the gantry assembly plus or minus 20 degrees from the vertical. The gantry assembly 10 carries the X-ray beam and detection equipment as well as the translational and rotational apparatus for manipulating the beam in the plane of the scan circle in the round gantry opening 14, approximately 20 inches in diameter. The servo motor controllers and associated apparatus which drive the gantry equipment are located in the scan power module 16 immediately behind the gantry 10. Also part of the typical CT scanner, although not shown in FIG. 1, are a display terminal, image processor, heat exchanger, X-ray power supply, scanner console and X-ray controls. These features form part of a standard "Delta Scan" TM system, currently marketed by the assignee of this application.

Figure 2:
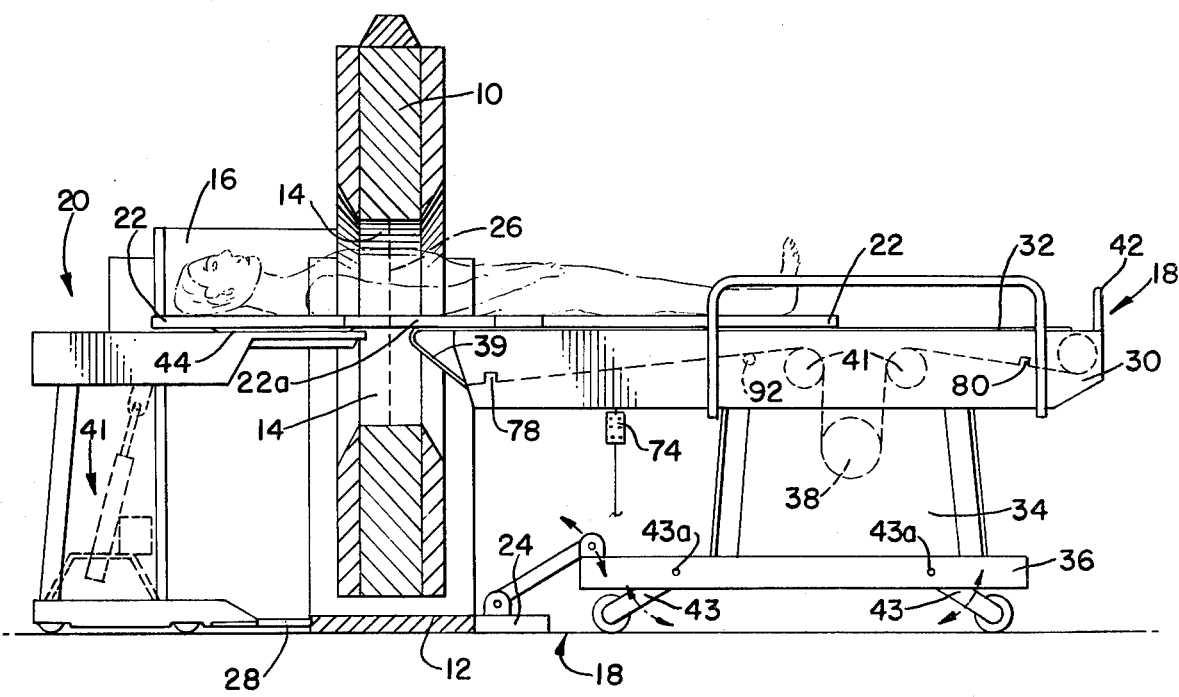
FIG. 2 is a side view of the patient support system for abdominal scans with portions of the CT scanner gantry broken away.
Figure 3:
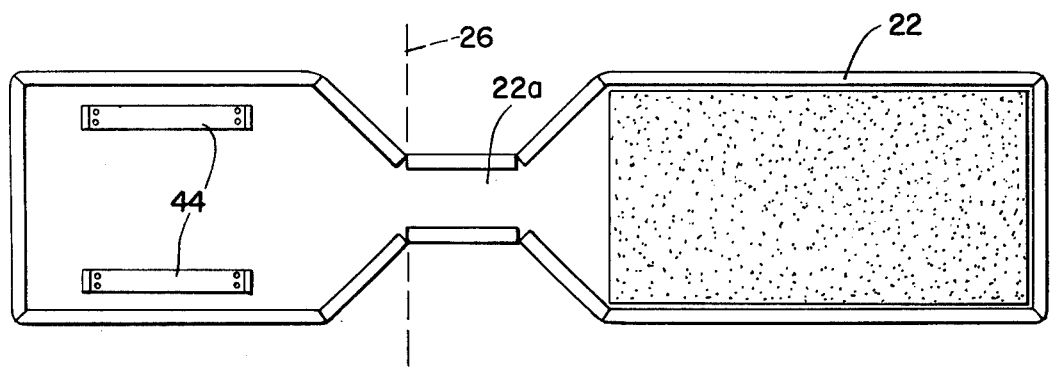
FIG. 3 is a plan view of the patient pallet for abdominal scans.
Figure 4:
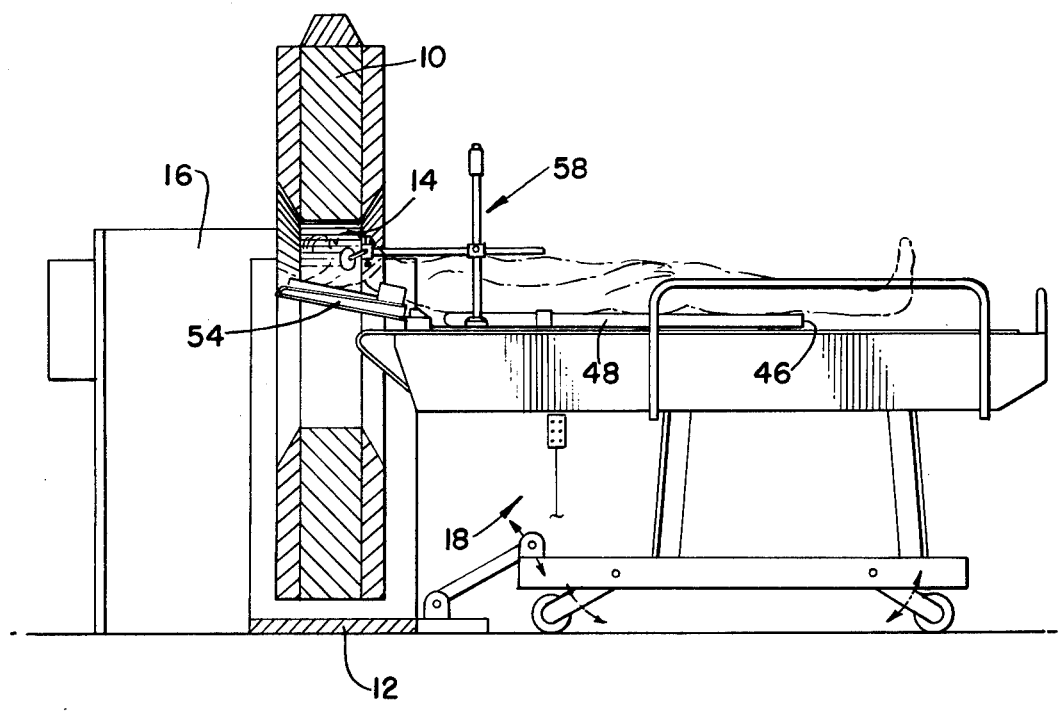
FIG. 4 is a side view of the patient support system for brain scans with portions of the gantry broken away.
Figure 5:
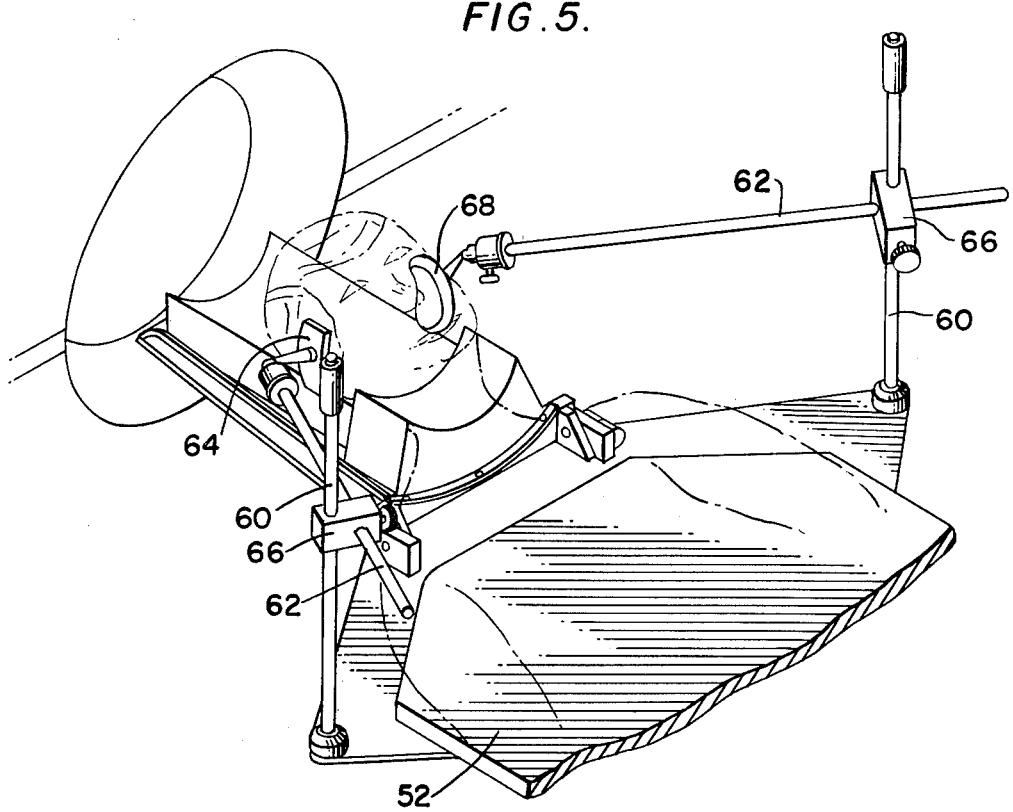
FIG. 5 is a detail perspective view of the check pad restraint members of the head restraint assembly in FIG. 4.
Figure 8:
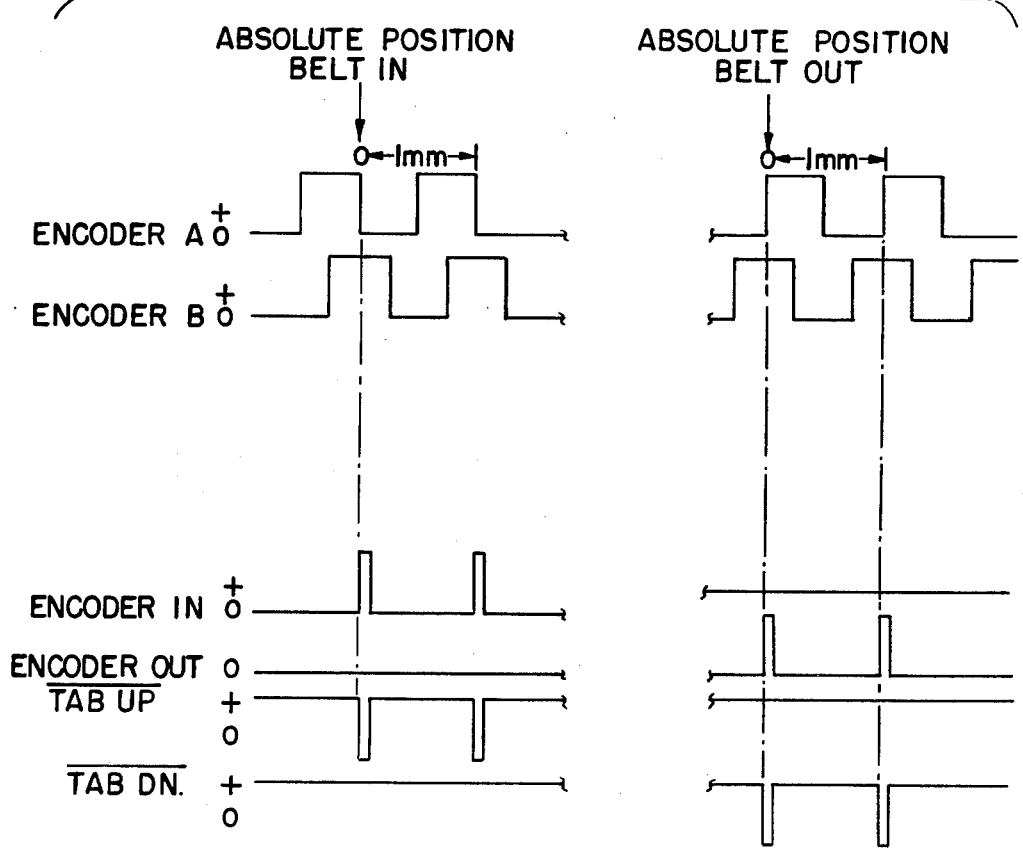
FIG. 8 is a waveform diagram illustrating typical encoder signals indicating belt travel.

FIGS. 1, 2 and 3 illustrate the physical features of the patient support system for abdominal scanning. The system for brain scans is shown in FIGS. 4 and 5 and 6 while a portion of the electronics for automatic table indexing, common to both brain and abdominal scans, is represented in FIGS. 7 and 8.

In FIGS. 1, 2 and 3 the patient support system for abdominal scans includes three separate elements: a wheeled front table 18, a smaller, wheeled rear table 20 and a thin, plastic and wood patient pallet 22. The front table is connected to the gantry support 12 by a detachable, pivotally mounted rigid link 24, in a position such that the projecting end of the front table barely extends into the gantry opening 14 without intersecting the scan circle plane 26 (FIG. 2). Similarly, the rear table is fastened to the gantry support 12 by a rigid detachable (nonpivoting) link 28 in substantial alignment with the front table, such that the cantilevered end of the rear table 20 proximate to the end of the front table 20, barely extends into the gantry opening 14 without intersecting the scan circle 26. The patient pallet 22 rests on top of and across the stainless steel tops of the front end and rear tables 18 and 20 such that its narrow-waisted section 22a spans the gap between the front and rear tables 18 and 20. Thus the section 22a is the only portion of the patient support system which intersects the scan circle. Consequently, besides air, the X-ray beams will encounter only the patient and a small volume of low density material in the patient pallet 22.

The front table 18 comprises a table top 30 with conveyer belt 32, cantilevered on a box-shaped support 34 housing a DC belt motor and reduction gearing (not shown), mounted on a wheeled carriage 36. The conveyer belt 32 is a single continuous loop with a hinged metal seam (not shown) driven by a drive drum 38 and tensioned by belt take up idler rollers 41. The drive drum is driven by the DC motor which is velocity controlled by a tachometer on the motor shaft and the motor control circuit, all commercially available. The table top 30 supports the conveyer belt at all points along the top path of the belt. The cantilevered end of the table top 30 adjacent to the gantry 10 includes a protruding stainless steel nose portion 39 over which the belt 32 rides. At the other end of the table top 30, the belt disappears through a slot 40. Conventional side guard rails are used on the front table as well as a failsafe bar 42 at the outermost end of the table top 30. The failsafe bar 42 actuates a microswitch which shuts down the system to prevent further excursion of the patient along the belt.

To accommodate tissue sections of different girth, the front and rear table 18 and 20 have separate elevational controls which allow the table tops to move up and down at a 30 degree angle to insure clearance from the gantry structure 10 when tilted a maximum of 20 degrees forward. Precise coplanarity of the tops of the front and rear tables 18 and 20 is not essential because of the flexibility of the pallet 22. The front table 18 must roll away from the gantry when the table 18 is being lowered to keep the front table from hitting the gantry when the top of the gantry is tilted toward the rear. This is accomplished automatically by pivoting the rigid link 24 at the bottom of the support structure 12. The top of the rear table 20 supported by linear bearings (not shown) is elevated on a 30° diagonal toward the gantry 10 by means of a linear drive system 41 with a ball screw and AC motor, while the entire front table 18 including the carriage 36 is raised by AC motor-driven wheel links 43 which pivot the wheels oppositely about respective axes 43a.

For abdominal scans, the patient pallet 22 is laid on top of the front table 18. The patient is positioned on the pallet 22 so that the section of the patient's body that is to be scanned is over the narrow-waisted part 22a of the pallet 22. The pallet is then driven by the conveyor belt 32 until the low friction skids 44 engage the stainless steel top of the rear table 20. The pallet 22 continues to be driven by the belt, with the pallet sliding over the rear table, until the patient is positioned for the first scan. The front and rear tables may be raised or lowered vertically under operator control in order to keep the patient centered in the gantry opening. The patient's weight on the pallet 22 causes sufficient friction between the high friction surface of the pallet 22 and conveyor belt 32 to allow the palleted patient to be moved back and forth through the scan circle 26.

For brain or head scans, the rear table 20 and patient pallet 22 are not used. Instead, as shown in FIGS. 4 and 6, a detachable unitary, restraint assembly 46 is used in conjunction with the front table 18 alone since all of the support for the patient's head can be accomplished from one side of the gantry 10. The head restraint assembly 46 includes a rectangular restraint body pad 48 with a safety belt 50 attached to a metal base plate 52 carrying a hinged, thin, plastic, contoured headrest 54 held in place by a ratchet hinge mechanism 56 and raised or lowered by hand. A pair of cheek pad restraint assemblies 58 are mounted on either side of the plate 52. Each restraint assembly 58 includes a vertical pole 60 with an articulated boom-like arm 62 having a pivoted cushion pad support 64 on one end. Knurled knobs on a holder 66 allow precise positioning of the cushion pads 68 against the patient's face as shown in FIG. 5.

For a brain scan, the head restraint assembly 46 is placed on the front table conveyor belt 32 instead of the patient pallet 22. The patient is placed on a restraint body pad 48 with his head in the headrest 54. The head is positioned at the prescribed angle by adjusting the headrest 54. Next, the cheek pads 64 are located on the patient's face and secured in position by means of the holder 66. The operator then energizes the conveyor belt drive motor, and the upper portion of the belt 32 moves toward the gantry opening 14 until the patient's head is located within the scan circle 26. The belt 32 may be moved in or out slowly for more precise positioning by manual controls as discussed below. The front table can also be raised or lowered separately to center the head tissue section in the scan circle 26.

For either brain or abdominal scains, the conveyor belt 32 provides axial positioning of the patient. The functions of the belt drive system are to advance the patient further into or retract the patient from the gantry opening, to recognize an extreme limit of travel in either direction and, in the automatic mode, to index the patient further out of the gantry opening by preestablished intervals, for example, 26 millimeters, after each one of a series of complete scans by the CT scanner. The latter function is the only one which requires a control signal from the image processor (not shown) of the CT scanner. This signal, designated for explanation herein as "SCAN OVER," is a signal internally produced by the image processor indicating that the procedure for one scan of the scan circle has been completed, the scanner is idle and the patient may be moved to another location for the next scan. The other functions reside solely in the table itself.

In FIG. 7 the table belt drive consists of a DC motor 70 driving a gear reducer (not shown) connected to the belt via a chain driven drum 38 (FIG. 2). The DC motor 70 is bidirectional and is driven by positive and negative high and low DC voltages to produce slow or fast forward or reverse rotation, i.e., inward, toward the gantry opening, or outward, from the gantry. The belt motor 70 is operated by a conventional belt motor controller 72 such as that manufactured by Cleveland Machine Control, Inc., or Graham, Inc. Typical voltages are +0.7 volts DC and +10 volts DC for slow and fast outward belt motion, respectively, and −0.7 volts and −10 volts DC for slow and fast speed inward belt motion.

Manual belt control 74 can be employed by the operator (see FIG. 2) to energize the belt motor 70 via a selectable analog control voltage source 76 to which the motor controller 72 is responsive. The metal seam joining the ends of the continuous belt 32 is designed to be located below the top of the table 30 in FIG. 2 at all times to insure patient comfort and to utilize the seam in a limit switching function. Metal proximity sensors 78 and 80 are located at either end of the table top 30 to sense the passage of the metal seam. The seam travels between the sensors 78 and 80 on the underside of a loop and are never indexed to the top of the table. Accordingly, the seam sensor 78 indicates the outer limit of travel of the belt along the top of the table away from the gantry opening 14. Likewise, the seam sensor 80 establishes the inner limit of travel of the belt on the top of the table toward the gantry opening 14. In either case, the sensing of the seam causes respective one shot (monovibrator) circuits 82 and 84 in FIG. 7 to actuate respective magnetic latching relays 86 and 88. The relays 86 and 88 remain latched even if power is turned off to insure that the machine will remember that it is at the limit when it is turned on the next time. If the belt is at its outer limit, the logic output of the latching relay 86 produces an input to the selectable analog control voltage circuit 76 to disable the production of the BELT OUT signal at either the fast or slow speed. However, operating the belt manually in the IN direction automatically resets the relay 86. Similarly, if the belt has reached the inner limit, the corresponding relay 88 disables the BELT IN signal, and operation of the belt in the outward direction automatically resets the relay 88.

The position of the belt 32 is indicated to the operator by a belt travel indicator system 90. A table position incremental rotary encoder 92 (FIG. 2) dirven by the belt near the drive drum 38 on the underside of the table top 30 provides distance information as to how far the belt has moved. The encoder circuit 92a (FIG. 7) interprets belt travel by creating phased ENCODER A and ENCODER B signals as shown in FIG. 8. These signals are directionally encoded to insure that a pulse for every millimeter of belt travel will occur at the same absolute position of the encoder (belt). According to the direction of rotation, the encoder B output enables a trailing edge pulse on the A output to trigger the count up one-shot (included in enocder circuit 92a) and the B output enables a leading edge pulse to trigger the count down singal. The count up and count down signals are labeled TB UP and TB DN. In FIG. 7 the TB up and TB DN signals are sent to the increment and decrement inputs respectively of the digital up/down counter 94. The output of the counter 94 is passed via a decoder/driver circuit 96 to a numerical display 98 located on the table top 30 alongside the belt 32 as shown in FIG. 1.

The indicator 98 shows, preferably in millimeters, how far the belt has moved from wherever the operator depressed the zero reset button for the first scan. This allows the operator to position a patient for the first scan a precise distance from a convenient or customary anatomical reference, e.g., the O-M line on the head, and then by operating the manual table controls to move the patient a measured distance to a second scanning position. This procedure is used for either brain or abdominal work.

Regardless of the reading on the table display, if the seam sensor 78 indicates that the outer limit has been reached, the corresponding output of the latching relay 86 will advise the decoder/driver 96 to display an "H" corresponding to the "home" position. Likewise, the output of the latching relay 88 is used to indicate that the inner limit has been reached by displaying an "I."

It is often desirable to make numerous adjacent scans. Iterative incrementing of the axial position of the patient can be carried out automatically. Since CT scanning systems require software capabilities for processing images, the computer which processes the images can be borrowed to serve as a programmable controller for the automatic table out function since it requires minimum storage. Thus, the programmed computer in the image processor would interrogate the console switches and at the appropriate time in the scan procedure, signal the belt drive to start moving in the out direction. When the digital distance information from the encoder on the belt matches the programmed distance in the computer, the computer would signal the belt drive to stop. This operation is represented in FIG. 7 in an operative hardware form for the sake of explanation of the functional requirements. The counting, comparing and switching functions, of course, can be carried out by software, if desired.

The system of FIG. 7 causes the belt to move in the outward direction at slow speed for a predetermined distance after each successive scan has been completed. The pulses which increment the counter 100 are the TB DN (belt out) pulses form the table position encoder circuit 92a. When the image processor determines that the scan procedure at a given location is complete, the processor issues a SCAN OVER signal. This logic signal resets the counter 100 to zero. The SCAN OVER signal is also connected to the set input of an R-S flip-flop 104. Changing of the SCAN OVER line from low to high sets the flip-flop 104 input labeled AUTO TABLE OUT which is passed to the selectable analog control voltage circuit 76 which causes the belt to begin to move slowly in the outward direction under the control of the belt motor controller 72. While the belt is moving, TB DN pulses are being produced by the encoder circuit 92a. Each one of these pulses increments the counter 100 one unit. The output of the counter 100 is fed to a comparator 102 provided with a reference count by the latch 103. The belt continues to move and the counter 100 continues to count up until its count matches the reference count and the comparator 102 issues a STOP signal. The STOP signal is passed via an OR gate 106 to reset input of the flip-flop 104, resetting the flip-flop and removing the AUTO TABLE OUT signal to stop the belt motor 70. The STOP signal from the comparator 102 is also fed back to the image processor to indicate to the CT scanner that the patient is ready for the next scan. As a precaution, a timer 107 started by the AUTO/OUT signal will reset the flip-flop 104 after a maximum allowable interval. Without any other type of control function, this incrementing of the patient's axial position and the taking of successive scans could continue until the seam sensor 78 senses the outer limit. At that point, the output of the latching relay 86 through the OR gate 106 would reset the flip-flop 104 to remove the AUTO TABLE OUT signal even if the comparator 102 had not yet issued its STOP signal. In addition, the outward motion of the belt 32 would be disabled directly by the DISABLE BELT OUT signal to the analog control voltage circuit 76. As a further precaution because of the use of an automatic mode for patient transport, a failsafe bar switch 42a can be tripped by the patient's feet at the end of the table to remove the AUTO TABLE OUT signal and to disable belt motion in the outward direction.

Instead of allowing the circuitry to increment axial position indefinitely up to the limit, the control system can lock after a predetermined number of increments, for example, by counting STOP signals. This implementation would allow the operator to determine a central plane, for example at 520 millimeters, and then back up six increments and set the number of increments at 13 in order to cover an equal volume of tissue in front of and behind the central plane.

The invention may be embodied in other specific forms without departing from its spirit or essential characteristics. The present embodiments are, therefore, to be considered in all respects as illustrative and not restrictive, the scope of the invention being indicated by the claims rather than by the foregoing description, and all changes which come within the meaning and range of the equivalents of the claims are, therefore, intended to be embraced therein.

What is claimed is:

1. A patient support system for locating a desired part of the body in a predetermined planar area with minimal intersection of said area by said support system, comprising:
movable front and rear tables;
means for aligning said tables on either side of said planar area at a predetermined spacing;
a patient pallet resting on the top of at least said front table;
drive means located on said front table for propelling said patient pallet in either axial direction along the top of said tables; and
failsafe bar switch means located at the end of at least one of said tables away from said planar area and positioned to be tripped by a patient's feet, means responsive to the tripping of said failsafe switch means for stopping said drive means in order to prevent the drive means from propelling said patient pallet with said patient to a position where said patient is not adequately supported.

2. The system of claim 1, wherein said pallet has an intermediate segment of diminished width adapted to the positioned, when in use, across the gap between said tables and said pallet is thin and has a low density.

3. The system of claim 1, wherein said front and rear tables are equipped with separate elevational drives.

4. The system of claim 1, further comprising a control circuit for automatically incrementing the position of a patient on the pallet a predetermined interval in response to a control signal.

5. The system of claim 1, further comprising a separate removable patient head restraint assembly adapted to be used in conjunction with only said front table, said assembly including an articulated headrest and a body pad connected thereto, said assembly being positionable on said front table with said headrest extending through said planar area, said drive means of said table engaging said body pad.

6. The system of claim 5, wherein said drive means is a continuous conveyor belt.

7. The system of claim 1, wherein said drive means is a continuous conveyor belt.

8. The system of claim 7, further comprising means for indicating the position of said belt along the top of said table.

9. The system of claim 8, wherein said indicating means includes an encoder, for providing output pulses indicative of belt travel, resettable counter means for counting said encoder pulses and a numerical display located on said front table operatively displaying the output of said counter means.

10. The system of claim 7, further comprising switch means arranged on said front table for sensing the passage of a predetermined part of said belt, means responsive to the condition of said switch means for indicating the outer limit of belt travel.

11. The system of claim 10, wherein said belt has a hinged metal seam, said switch means being responsive to passage of said seam.

12. The system of claim 10, further comprising another switch means located on said table and spaced along said belt from said one switch means, for detecting passage of said predetermined part of said belt, means responsive to the condition of said other switch means for indicating the inner limit of belt travel.

13. The system of claim 12, wherein said belt has a hinged metal seam, both said switches being responsive to the passage of said seam for producing output signals.

14. A patient support system for use with a CT scanner or the like with an image processor, said CT scanner having an intrinsic scanning circle, comprising:
movable front and rear patient tables;
means for aligning said tables on either side of said scanning circle with a predetermined gap;
a removable, thin, low density patient pallet positionable across said front and rear tables through said scanning circle with an intermediate segment of reduced width at the gap between said tables;
said front table being operatively equipped with a continuous conveyor belt for engaging the underside of said pallet, said patient pallet being adapted to slide on the surface of said rear table;
a bar located transversely across an end of said table;
drive means for causing said belt to move said pallet in an axial direction through said scanning circle;
control means responsive to an idle signal from said image processor for causing said motor to increment the axial position of a patient on said pallet by a predetermined distance and for signaling said image processor to begin the next scan when the position of said patient has been thus incremented; and
failsafe switching means operatively connected with said bar and said control means for disabling the drive means in response to an interaction of the patient and the bar to prevent the drive means from propelling said patient pallet with said patient to a position where said patient is not adequately supported.

15. The system of claim 14, wherein said control means increments the position of said patient by moving said belt in a direction away from said scanning circle.

16. The system of claim 14, further comprising a removable head restraint assembly usable in conjunction with said front table having a base with an articulated headrest on one side and a body pad attached to the other side adapted to be positioned on and driven by the belt on said front table such that said headrest intersects said scanning circle.

17. The system of claim 16, wherein said CT scanner includes a tiltable gantry assembly defining said scanning circle, said means for aligning said tables including a pivoted link between the bottom of said tiltable gantry support assembly and one of said tables to automatically displace said table in an axial direction whenever said table is vertically moved.

18. A patient support system for use with a CT scanner or the like with an image processor, said CT scanner having an intrinsic scanning circle, comprising:
   at least one patient table alignable with said scanning circle;
   a foot bar located transversely across an end of said table;
   a belt operable in conjunction with the patient table for transporting a patient on the patient table through the scanning circle;
   drive means for causing the conveyor belt to move;
   control means responsive to a signal from the image processor causing the drive means to increment the axial position of the conveyor belt by a predetermined distance and for signaling the image processor to begin the next scan when the position of the patient has been incremented; and
   failsafe switching means operatively connected with said foot bar and said control means for disabling said drive means to prevent moving said patient to a position where said patient is not adequately supported.

* * * * *